United States Patent [19]

Saunders

[11] 4,361,554

[45] Nov. 30, 1982

[54] ORGANIC INSECTICIDE

[75] Inventor: Tom R. Saunders, Wimberly, Tex.

[73] Assignee: Texas Botanical Research, Company, Kerville, Tex.

[21] Appl. No.: 261,002

[22] Filed: May 6, 1981

[51] Int. Cl.³ .................... A01N 31/00; A01N 65/00
[52] U.S. Cl. .................................... 424/180; 424/195
[58] Field of Search ................................ 424/195, 180

[56] References Cited

U.S. PATENT DOCUMENTS

| | | | |
|---|---|---|---|
| 287,701 | 8/1883 | Miller | 424/195 |
| 2,082,952 | 6/1937 | Gruwell et al. | 424/195 |
| 2,301,787 | 11/1942 | Nord | 424/195 UX |
| 3,227,616 | 1/1966 | Van Wessem et al. | 424/361 |

OTHER PUBLICATIONS

McIndoo, "Plants of Possible Insecticidal Value", 1945 (U.S.D.A) S.L. SB107M3, pp. 55, 104, 256 & 286.

*Primary Examiner*—Donald B. Moyer
*Attorney, Agent, or Firm*—Littlepage & Webner

[57] ABSTRACT

A composition based on extract from cacti is used as an insecticide against soft bodied insects injurious to plants. A process for preparing the extract and its use as an insecticide are given.

1 Claim, No Drawings

ORGANIC INSECTICIDE

BACKGROUND OF THE INVENTION

There are many commercial insecticide preparations highly effective against insects. However, it has been amply demonstrated that these preparations are generally extremely lethal even in small quantities and persistent in the food chain. For these environmental concerns it is preferable to seek alternatives devoid of these properties. Unfortunately, alternative choices have not been as effective as desired and also not devoid of the injurious effects on the environment.

PRIOR ART STATEMENT

Cactus extracts, particularly "prickly pear" (Opuntia Phaeacantha) have been suggested for medicinal purposes.

U.S. Pat. No. 2,082,952 teaches that prickly pear extract is effective in reducing carbohydrates in the blood stream of humans and thereby has efficacy against diabetes.

U.S. Pat. No. 367,406; 604,111 and 65,580 also show cactus as one ingredient in various medicinal preparations for human use.

SUMMARY OF THE INVENTION

An insecticide composition composed of cactus extract in a solvent is effective against nonexoskeletal insects such as spider mites, mealy bugs, aphids, thrips, white flies and insect eggs and larvae. The composition may be prepared in advance and preserved, preferably using tannic acid.

The composition is prepared by grinding the cacti into a mulch. Subsequent compression yields a fluid extract. The extract is filtered and impurities removed. Heating to about 212° F. for a short period concludes the process. Tannic acid is added after cooling to about 150° F.

Generally the extract is prepared to be about 8–12% of the insecticide composition, but preferably is applied to the plants in amounts such that the extract is about 10% of the solution.

Remarkably, the preparation has proven to be highly effective against soft-bodied insects yet no indication of toxicity to plants or animals has been found.

DETAILED DESCRIPTION OF THE INVENTION

THE CACTI

Genera of cacti such as Echinocactus, Cereus, Opuntia and Pereslicia produce extracts which are useful as an insecticide, but with varying effectiveness.

Cacti species from the genera Opuntia (prickly pear) are preferred. Representative species, commonly found in the southwestern parts of the United States are O. durangensis and Ocompressa. The species O. Phaeacantha is preferred based on its effectiveness and availability.

All parts of the cactus may be harvested and used to prepare the mulch. The extract, as prepared by the process discussed below, is conveniently stored as a solution generally 8 to 12%, preferably 10% by weight of the total solution. The solvent selected for the extract may be chosen from a variety of solvents in which the extract is soluble, such as water, alcohol and hydrocarbon distillates. Water is preferred, for its availability, cost and ease of solubilizing. The extracts storage requires the inclusion of a preservative.

PRESERVATIVE

The use of a preservative is preferred in order that the solution may be prepared in advance.

Preservatives other than tannin may be employed.

The tannin inhibits fermentation of the cacti juice. Also the extract, once applied to the plant is effective for longer periods if tannin is included in the composition.

Tannin is a preferred preservative. An amount sufficient to act as preservative for periods up to a year are suggested. This amount can vary between 0.1 and 0.5%, 0.3% is preferred. However, lesser amounts are less effective and greater amounts unnecessary and wasteful.

The vegetable tannins are commercially available from Mallinkrodt, Inc., St. Louis, Missouri. A wide variety of commercially available tannins may be used. For a discussion of tannins, see Encyclopedia of Chemical Technology, 2nd edition, Kirk-Othmer; XII (1967) pp. 303–341.

Tannins are generally characterized as polyphenolic substances having molecular weights of from about 400 to about 3000. They may be classified as "hydrolyzable" or "condensed" depending upon whether the product of hydrolysis in boiling mineral acid is soluble or insoluble, respectively. Often, extracts are mixed and contain both hydrolyzable and condensed forms. No two tannin extracts are exactly alike. Principal sources of tannin extracts include bark such as wattle, mangrove, oak, eucalptus, hemlock, pine, larch, and willow; woods such as quebracho, chestnut, oak, and urunday, cutch, and turkish; fruits such as myrobalans, valonia, dividivi, tera, and algarrobilla; leaves such as sumac and gambier; and roots such as canaigre and palmetto.

The term "vegetable tannin" is employed to distinguish organic tannins such as those listed in the previous paragraph from the mineral tannin materials.

Hydrolyzable, condensed and mixed variations of vegetable tannins are suitable for the present invention. Oak bark tannin is typically used.

SOLVENT

Water, alcohols, and hydrocarbon distillates are possible solvents for the extract and extract plus tannin. The only requisites are that the solvent solubilize the active components, be inert in use and harmless to the applied plants. Water, for reasons of excellent solubility, availability and cost is preferred.

OTHER INGREDIENTS

Optional ingredients may be added to the essential component of the concentrate. In addition to the preferred preservative, dyes and surfactants are often added for the convenience of applying the insecticide especially in spraying applications.

EFFECTIVE AGAINST INSECTS

In order for the novel insecticide to be effective it must be able to penetrate into the insect. For this reason it is not effective against insects which have an exoskeleton. However, it can still be used against this type of insect in the egg and larval stages when the exolskeleton is absent.

The number of species of insects which have no exoskeleton is extensive; mosquitos, silverfish, termites, flies, aphids, mealy bugs, and maggots, for example.

Aphids and mealy bugs are injurious to many cultivated plants. The insecticide has been tested particularly on these insects and results are exceedingly good.

Comparisons of the novel insecticide with known commercial products show that the novel insecticide is just as effective in killing the aphids with no injury to the plant.

PROCESS FOR PREPARING THE EXTRACT

The cacti are harvested, drained and sized for the feed hopper of a hammer mill. The cacti pieces may be stored for short periods (up to a week), but fresh cacti are preferred. The hammer mill reduces the cacti to a mulch.

The mulch is subjected to high pressure in order to extract a fluid extract. Hydraulic compression is conveniently employed.

The fluid is filtered and conveyed to a sedimentation tank. After 2 to 24 hours most impurities have settled out. The purified extract is heated to about 212° F. for about 2 minutes. After cooling to about 150° F., the preservative, typically tannic acid from oak bark, is added.

The concentrate extract is bottled and refrigerated.

The following examples illustrate the invention and present the best mode contemplated for practicing the invention.

EXAMPLE 1

This example is illustrative of producing the extract. Fifty lbs of opuntia cactus, species Opuntia Phaeacantha is ground into a mulch as described above. The mulch is hydraulically compressed and 401 lbs. of extract produced. Ten gallons of water is added and mixed. The extract is filtered and passed to a sedimentation tank and held for 24 hours for the impurities to settle out.

The purified extract is heated for 2 minutes at 212° F. and cooled to 150° F. A quantity of 0.2% of tannic acid (source-commercial) is added. The solution is bottled and refrigerated.

EXAMPLE 2-4

The procedure of example 1 is followed with the exception that in Example 2, O. bergeriana species is used; in Example 3 O. compressa species; and for Example 4 O. durangensis species.

EXAMPLE 5

The procedure of Example 1 is followed with the single exception that no tannic acid is added to the extract.

The extracts prepared in Examples 1-4 are made up in the following concentrations shown in Table 1:

TABLE 1

| Solution No. | Extract from Example | % extract | % tannin* | % water |
|---|---|---|---|---|
| A | 1 | 8 | .2 | 91.8 |
| B | 1 | 10 | .3 | 89.7 |
| C | 1 | 12 | .3 | 87.7 |
| D | 2 | 10 | .3 | 89.7 |
| E | 3 | 10 | .3 | 89.7 |
| F | 4 | 10 | .3 | 89.7 |
| G | 5 | 10 | | 90.0 |

*tannin % can be adjusted in concentrate or in prepared solution.

TESTS

The solutions of Example 1 are sprayed onto tomato plants infested with two spotted spider mites insects. Additionally, tomato plants are sprayed with a commercially available insecticide, Kelthane, from Dexol company.

The results are tabulated below in Table 2.

TABLE 2

| Solution | Plant Condition | Killed after 20 minutes | Killed after 2 hours |
|---|---|---|---|
| A | Excellent | 100% | |
| B | Excellent | 100% | |
| C | Excellent | 100% | |
| D | Excellent | 100% | |
| E | Excellent | 100% | |
| F | Excellent | 100% | |
| G | Excellent | 100% | |
| H (Commercial Insecticide) | Fair | 2% | 3% |

A decided advantage of the cactus extracts is the lack of toxicity to both the workers preparing the extract and the workers applying the extract.

The stock solutions of Table 1 can be infused with 50% water and dried in a solar dryer at no more than 180% F. The powder is collected and ground in a ball grinder. The powder can then be stored for great lengths of time. A teaspoon of the powder can then be added to a gallon of water with ¼ ounce of surfactant and sprayed.

In addition, the seeds of Opuntia can be ground with 10% fixed oil, 60% water and 20% dispersant. A teaspoon of this can then be added to the above gallon of spray. This greatly enhances the above formula to include exoskeleton insects.

I claim:

1. A method of eradicating soft-bodied insects including said insects, insect larvae and insect eggs by contacting said insects with an insecticidally effective amount of aqueous solution consisting essentially of a mixture of cacti extract of opuntia cactus present in an amount of 8% to 12% and tannin present in an amount of 0.1% and 0.5% by weight of total solution, said solution being prepared by compressing a mulch of said cactus to produce an extract thereof, adding water to the extract, heating the extract and water to boiling temperature, cooling the heated extract and water and then adding the tannin to the cooled solution.

* * * * *